United States Patent [19]

Hugemann et al.

[11] 4,425,117
[45] Jan. 10, 1984

[54] DEVICE FOR THE RELEASE OF SUBSTANCES AT DEFINED LOCATIONS IN THE ALIMENTARY TRACT

[75] Inventors: Berhhard Hugemann, Frankfurt am Main; Otto Schuster, Bad Soden, both of Fed. Rep. of Germany

[73] Assignee: Battelle-Institut e.V., Frankfurt am Main, Fed. Rep. of Germany

[21] Appl. No.: 326,825

[22] Filed: Dec. 2, 1981

Related U.S. Application Data

[63] Continuation of Ser. No. 167,845, Jul. 14, 1980, abandoned.

[30] Foreign Application Priority Data

Jul. 14, 1979 [DE] Fed. Rep. of Germany ....... 3928477

[51] Int. Cl.$^3$ ............................................. A61M 31/00
[52] U.S. Cl. ...................... 604/93; 604/890; 604/132
[58] Field of Search ............... 128/260, 222, 213 R; 604/131–135, 890, 93, 95, 54, 57

[56] References Cited

U.S. PATENT DOCUMENTS

| | | | |
|---|---|---|---|
| 3,057,344 | 10/1962 | Abella | 128/2 |
| 3,118,439 | 1/1964 | Perrenoud | 128/2 |
| 3,315,660 | 4/1967 | Abella | 128/2 |
| 3,485,235 | 12/1969 | Felson | 128/2 |
| 3,659,600 | 5/1972 | Merrill | 128/172 |
| 4,239,040 | 12/1980 | Hosoya et al. | 128/213 |

Primary Examiner—Kyle L. Howell
Assistant Examiner—John C. Hanley
Attorney, Agent, or Firm—Fisher, Christen & Sabol

[57] ABSTRACT

A device for the release of a substance at a defined or desired location in the alimentary tract. The device has a capsule having a separating wall therein, which forms a first chamber and a second chamber in the capsule. A hole is present in the wall of the first chamber. A compression spring, that is in a compressed state, is affixed to a body located in the second chamber. A needle is mounted on the compression spring facing the separation wall. A resonant circuit, in the second chamber, is tuned to an electromagnetic field of high frequency. The resonant circuit has a coupling coil, positioned around the body, a capacitor, connected to the other end of the coil and extending away from the first chamber, and a resistance wire, attached to the coupling coil and the capacitor. A fuse wire is connected to the compression spring, extends through the longitudinal passageway of the body and is connected to the body end facing away from the first chamber. The fuse wire contacts the resistance wire. A balloon in the expanded state is positioned in the first chamber. When the device is subjected to an external electromagnetic field having the high frequency to which the resonant circuit is tuned, the fuse wire heats up and breaks. The compressed spring is released pushing the point of the needle through the separating wall and the balloon, which bursts releasing any substance contained in the first chamber.

5 Claims, 4 Drawing Figures

DEVICE FOR THE RELEASE OF SUBSTANCES AT DEFINED LOCATIONS IN THE ALIMENTARY TRACT

This is a continuation of application Ser. No. 167,845, filed July 14, 1980 now abandoned.

BACKGROUND OF THE INVENTION

1. Field of the Invention

This invention relates to a device for the release of substances at defined locations in the alimentary tract.

2. Prior Art

In human and veterinary medicine, taking medicines orally in the conventional manner can lead to undesired results, particularly when specific local treatment of certain parts of the alimentary tract is necessary. One of the major drawbacks is that the medicine, due to prior decomposition or digestion, cannot produce any effect at the diseased location, or even that it produces a harmful effect. Neither absorption areas nor absorption intensities can be determined using the methods normally used at present. A preparation enclosure which does not dissolve immediately because of its chemical composition and the thickness of the layer is also unfavorable since the pH values and action of the intestines which differ from case to case make controlled administration difficult. The introduction of medicines through a tubular probe represents a major burden for the organism and is therefore only possible in exceptional cases.

BROAD DESCRIPTION OF THIS INVENTION

The object of this invention is to create a device which can be filled with any substance, and which releases the substance at predetermined locations as it passes through the alimentary tract.

It has now been found that this object can be achieved in a technically advanced manner if the device is designed in the form of a capsule that can be swallowed and that can be opened by the effect of an external electromagnetic field.

The capsule according to this invention releases the active substance contained in the capsule in response to an external signal. The shape and dimensions of the capsule correspond to those of conventional medicine capsules so that it can be swallowed. For a capacity of, for example, 1 ml of active substance the external diameter of the complete capsule including the release mechanism and the active substance compartment is about 12 mm, and the length is ca. 25 mm. The capsule passes from the stomach into the intestines and is finally excreated with the stool.

If such a capsule is administered to the patient, its position as it passes through the alimentary tract can be determined by means of X-rays or ultrasonic inspection. By the effect of an electromagnetic field on the corresponding part of the body the capsule is opened precisely at a predetermined location, as it were by remote control, and the drug is released. In a preferred embodiment of this invention the opening mechanism is triggered off by a resonant circuit formed by a resistance wire, a coil and a capacitor. The resonance frequency is predetermined by proper dimensioning of the coil and the capacitor so that the effect of a high frequency field of a transmitter oscillating at the same frequency causes the resistance wire to be heated. An HF transmitter of the known kind, modified in that it features a coupling coil dimensioned to suit the body of the patient, can be used to apply the high frequency field. If the resonant circuit in the capsule is set at, for example, 4 MGz, an HF transmitter with an output of ca 20 Watts is normally sufficient to open the capsule.

According to one embodiment of this invention the capsule has a space which is limited by the cap of the capsule on the one hand and the piston on the other. The capsule cap is connected to the piston. The piston is moved toward the capsule cap by a compression spring when, after heating of the resistance wire, the fuse is triggered off. The fuse has been used to bend the compression spring into the compressed state. The fuse, for example, can be a synthetic thread.

In another embodiment the liquid or powder-form or spherical substance is filled or inserted into a balloon in the capsule. The opening mechanism acts on a needle which pierces the balloon. After the abrupt bursting of the balloon the substance is released through suitable openings, holes or slots in the capsule enclosure.

DETAILED DESCRIPTION OF THIS INVENTION

In the following, this invention is illustrated in further detail using diagrams representing a single embodiment. In the diagrams or drawings, shown in simplified form:

Figure 1:
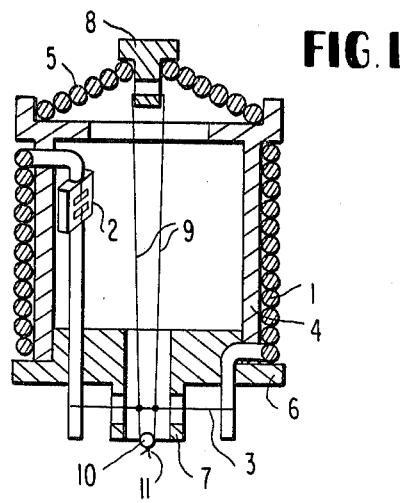
FIG. 1 is a partially-cutaway side elevational view of an resonant circuit arrangement which is fitted into the capsule.

As shown in FIG. 1 the resonant circuit consists of coil 1, e.g., constructed of copper wire, capacitor 2 and resistance wire 3. Resonant circuit copper wire coil 1 is fitted on to bobbin 4. The latter is designed in such a way that it serves simultaneously as a mounting for bell-shaped spring 5 and capacitor 2. The other end of bobbin 4 is closed by lid 6 through which the connecting wires of coil 1 and capacitor 2 are passed. Resistance wire 3 is connected to these wires and is passed through a cross hole in shaft 7. Thread 9, that melts easily, e.g., constructed of Perlon, is passed through a further longitudinal hole in shaft 7, through the hole in plastic nipple 8, back past toggle 10 and joined in knot 11. However, before tieing thread 9 is first tightened so as to bend bell-shaped spring 5. By turning toggle 10 on shaft 7, thread 9 is adjusted so that both sides of thread 9 touch resistance wire 3. If thread 9 is melted through by resistance wire 3, the force of bent bell-shaped spring 5 becomes effective, which opens the capsule and ejects the preparation.

Figure 2:
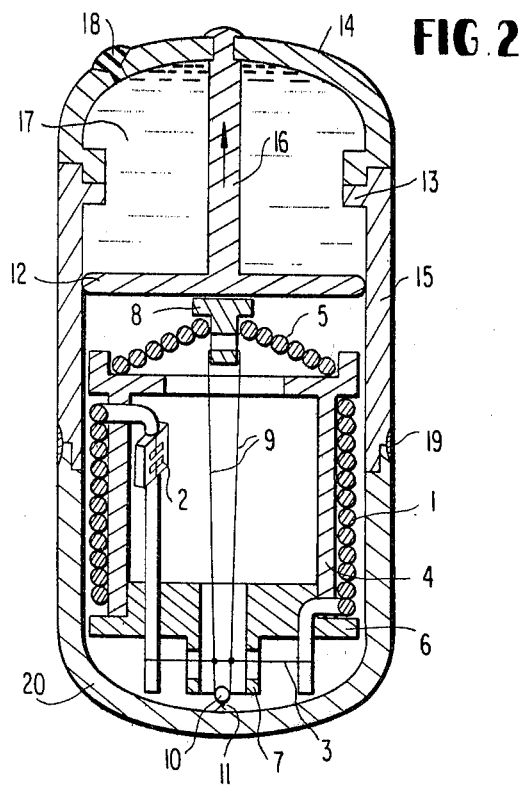
FIG. 2 is a partially cutaway side elevational view of the embodiment of FIG. 1, further including the capsule, with the resonant circuit (shown in FIG. 1) incorporated therein which is used as the opening mechanism.

FIG. 2 shows the schematic overall view of the capsule of this invention embodying the resonant circuit arrangement of FIG. 1. The spring power of bell-shaped spring 5, released after severance of thread 9, acts via plastic nipple 8 on piston 12, moving it in the direction indicated by the arrow up to limit stop 13. Since capsule cap 14 and piston 12 are joined by means of the spacer after being fitted into center part 15, capsule cap 14 also moves, thus opening preparation compartment 17. For filling the preparation into the capsule, opening 18 is provided in the upper section; this opening is designed in such a way that it can easily be sealed by a stopper or by sealing. Capsule cap 14 is leak-proof, but is fitted onto center part 15 of the capsule such that it is easy to separate the two parts. The other end of center part 15 is inseparably sealed to lower part 20 of the capsule by means of watertight seal 19.

All capsule and bobbin parts are made from a material that meet medical requirements.

Figure 3:
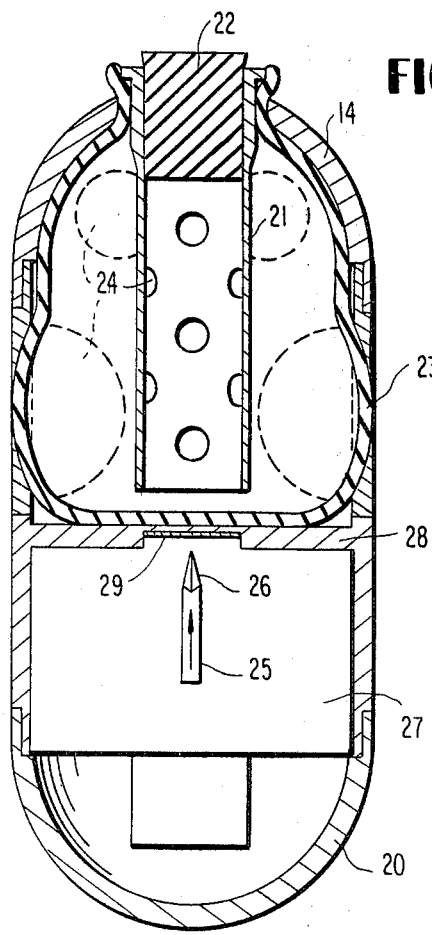
FIG. 3 is a partially-cutaway side elevational view of a further embodiment of this invention in which the active substance is in a balloon.

As shown in FIG. 3 the capsule has tubular mounting 21 which is sealed by rubber stopper 22. Latex molding 23, which forms the balloon, is fixed to mounting 21 and located beneath capsule cap 14. Mounting 21, capsule cap 14 or capsule enclosure 20 are provided with holes or slots 24 in appropriate places to permit the substance to escape or be ejected rapidly. Needle 25, preferably having additional cutting edges 26, is centrally positioned in propulsion mechanism 27. Additional cutting edges 26 permit not only a piercing effect but also a cutting one, ensuring that balloon 23 bursts and the substance is abruptly released. The tip of the needle is located below separating wall 28 of the capsule. In the center of separating wall, 28, i.e., in the piercing range of the needle, is located opening 29 which can be closed by a film. When needle 25 is released it pierces first the film in the region of opening 29 and then latex molding 23, causing the latter to burst abruptly and thus release the enclosed substance through the slots or holes in enclosure 14.

Figure 4:
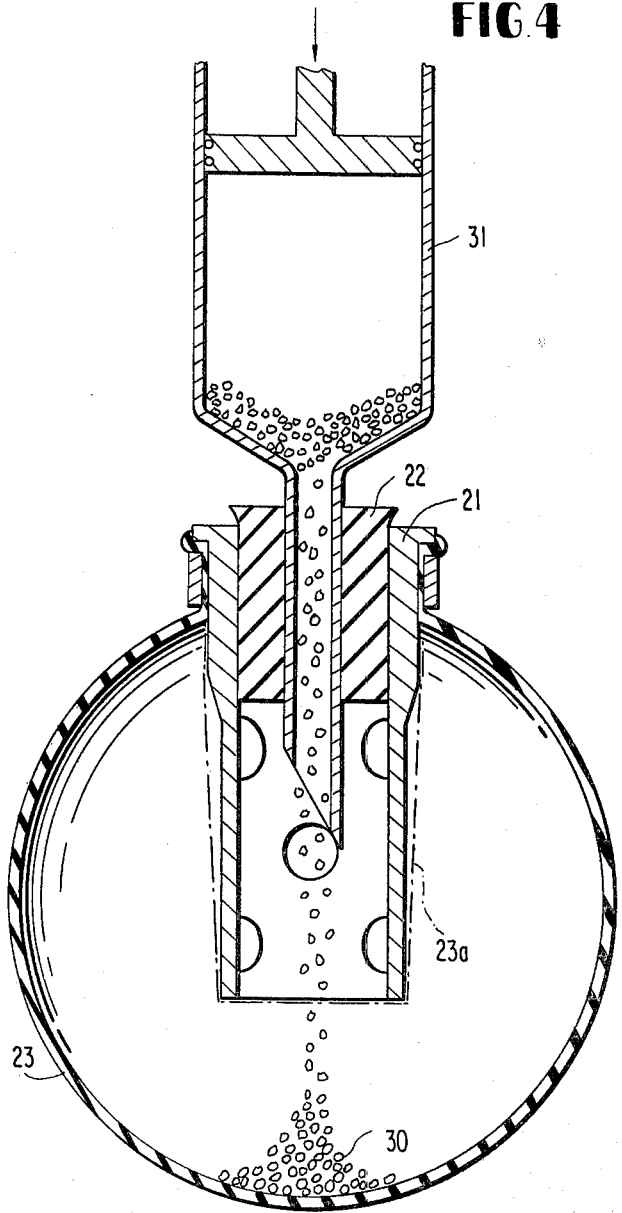
FIG. 4 is a partially-cutaway side elevational view of the filling the capsule of the embodiment shown in FIG. 3 with the active substance.

FIG. 4 shows in schematic form the filling of the substance into the device shown in FIG. 3. Both liquids and powders can be filled into balloon 23. If balloon 23 is filled with an active substance in powder form 30, air must first be blow into balloon 23 so that the substance can trickle into balloon 23 from hyperdermic needle 31 according to the principle of an egg-timer. For a volume of about 1 ccm, mounting 21 is preferably 13 mm to 14 mm in length so that balloon 23 remains in the piercing range of needle 25 even if small quantities of the substance are used and balloon 23 is not optimally extended. Stopper 22 of tubular mounting 21 is preferably made from a material that closes up the opening from the piercing of hyperdermic needle 31 automatically once needle is removed.

Certain particularily advantageous embodiments of this invention are set out in the following. In the device for the release of substances at defined locations in the alimentary tract, the electric field can be produced by using an HF transmitter with coupling coil that is adapted to suit the body. Also, in capsule 14, 15, 20, resistance wire 3 can be combined with fuse 9 which serves to bend compression spring 5—the force of compression spring 5, which is released after the heating of wire 3 and the blowing out of fuse 9, which are associated with the use of an electromagnetic field, is used to discharge the substance from the capsule. Resistance wire 3 is part of a resonant circuit formed by coil 1 and capacitor 3. The coil of the resonant circuit can be designed to act simultaneously as a compression spring. The resistance wire is part of an arrangement consisting of the power source and the magnetically controllable switch. The force of compression spring 5 acts upon piston 12 which is linked to cap 14 of the capsule by means of spacer 16. Cap 14 of the capsule can be connected to the rest of capsule 15 by a plug-type connector and seals substance compartment 17—limit stop 13 is provided which determines the path of piston 12 when compression spring 5 is released. In a different embodiment, the active substance is stored in balloon 23 within capsule enclosure 14 which is provided with holes and slots 24. Needle 25 can be moved by the force of compression spring 5 in such a way as to pierce and burst balloon 23. The tip of needle 25 can be provided with additional cutting edges 26. Tubular mounting 21 can be connected with the upper part of balloon 23 or capsule enclosure 14 and sealed airtight from above. Mounting 21 can be provided with holes 24 and holds balloon 23 because of the appropriate dimensioning of the latter in the piercing range of needle 25 irrespective of the quantity of substance introduced into balloon 23.

We claim:

1. A device for the release of a substance at a defined or desired location in the alimentary tract, comprising:
   (i) a capsule having a separating wall therein, the wall being aligned approximately perpendicular to the longitudinal axis of the capsule, the wall forming a first chamber and a second chamber in the capsule, at least one hole or slot being present in the capsule in the region of the first chamber,
   (ii) a body that is positioned in the second chamber, the body having a longitudinal passageway therethrough which is approximately aligned with the longitudinal axis of the capsule,
   (iii) a compression spring that is in a compressed state and is located on the end of the body facing the separating wall,
   (iv) a needle that is mounted on the compression spring, extending out beyond the compression spring, and is aligned with the longitudinal axis of the capsule, having its pointed end facing the separating wall,
   (v) a resonant circuit that is located in the second chamber and that is tuned to a electromagnetic field of high frequency, the resonant circuit comprising (a) a coupling coil that is positioned around the body, one end of the coil extending away from the first chamber, (b) a capacitor, one side of the capacitor being connected to the other end of the coil, the other side of the capacitor extending away from the first chamber, and (c) a resistance wire attached to the end of the coupling coil and the side of the capacitor which extend away from the first chamber,
   (vi) a fuse wire that is connected to the compression spring, extends through the longitudinal passageway of the body and is connected to the end of the body facing away from the first chamber, the fuse wire being in contact with the resistance wire, and
   (vii) a balloon in the expanded state that is positioned in the first chamber, substantially all of the surface of the balloon being in contact with the first chamber, whereby, when the device is subjected to an external electromagnetic field having the high frequency to which the resonant circuit is tuned, the fuse wire heats up and breaks, and the compressed spring is released pushing the point of the needle through the separating wall and the balloon, which bursts, thereby releasing any substance contained in the first chamber.

2. Device as claimed in claim 1 wherein the pointed end of the needle is provided with cutting edges.

3. Device as claimed in claim 1 wherein the balloon has an opening, and a tubular mounting is positioned within the balloon, one end of the tubularm ounting extending through the opening in the balloon and the outside wall of said first chamber, and said end of said tubular mounting being sealed air-tight, the tubular mounting being provided with holes, and the tubular mounting holding the balloon within the piercing range of the needle irrespective of the quantity of the substance which may be contained in the balloon.

4. Device as claimed in claim 3 wherein the sealed end of the tubular mounting is sealed air-tight by means of a rubber stopper inserted in the sealed end.

5. Device as claimed in claim 1 wherein the portion of the separating wall adjacent to the pointed end of the needle is thinner than the rest of the separating wall.

* * * * *